(12) United States Patent
Goebel et al.

(10) Patent No.: US 7,763,196 B2
(45) Date of Patent: Jul. 27, 2010

(54) CATHETER

(75) Inventors: Udo Goebel, Melsungen (DE); Martin Sippel, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 11/875,296

(22) Filed: Oct. 19, 2007

(65) Prior Publication Data

US 2008/0045927 A1 Feb. 21, 2008

Related U.S. Application Data

(62) Division of application No. 10/175,455, filed on Jun. 18, 2002.

(30) Foreign Application Priority Data

Jun. 19, 2001 (DE) .............................. 201 10 121 U

(51) Int. Cl.
*B29C 47/06* (2006.01)
(52) U.S. Cl. ............................. 264/173.16; 264/209.5; 264/210.6
(58) Field of Classification Search ........................ None
See application file for complete search history.

(56) References Cited

U.S. PATENT DOCUMENTS

| | | | |
|---|---|---|---|
| 3,885,561 A | | 5/1975 | Cami |
| 4,211,233 A | * | 7/1980 | Lin .............................. 604/43 |
| 4,283,447 A | * | 8/1981 | Flynn ........................ 428/36.9 |
| 4,451,256 A | | 5/1984 | Weikl et al. |
| 4,557,721 A | | 12/1985 | Hooven |
| 4,639,252 A | | 1/1987 | Kelly et al. |
| 5,106,376 A | * | 4/1992 | Mononen et al. ....... 604/164.11 |
| 5,180,387 A | | 1/1993 | Ghajar et al. |
| 5,234,406 A | | 8/1993 | Drasner et al. |
| 5,308,342 A | | 5/1994 | Sepetka et al. |
| 5,496,294 A | | 3/1996 | Hergenrother et al. |
| 5,533,985 A | | 7/1996 | Wang |
| 5,599,326 A | | 2/1997 | Carter |
| 5,611,778 A | | 3/1997 | Brinon |
| 5,614,136 A | * | 3/1997 | Pepin et al. ................. 264/40.3 |

(Continued)

FOREIGN PATENT DOCUMENTS

EP 0 437 291 B1 7/1991

(Continued)

OTHER PUBLICATIONS

Office Action mailed Feb. 10, 2009 from corresponding U.S. Appl. No. 10/175,455.

(Continued)

*Primary Examiner*—Monica A Huson
(74) *Attorney, Agent, or Firm*—Klein, O'Neill & Singh, LLP

(57) ABSTRACT

The catheter provided in accordance with aspects of the present invention includes an elongate tube having a proximal tube portion and a distal tube portion formed by stretching the distal portion of the elongate tube. The catheter is made throughout from an identical material. The distal tube portion has a reduced outer diameter and thus is of a higher flexibility and softness. Therefore, the danger of injuries to vessels or the dura is decreased. The catheter can be produced in an inexpensive and simple manner.

19 Claims, 2 Drawing Sheets

U.S. PATENT DOCUMENTS

| | | | |
|---|---|---|---|
| 5,700,252 A | 12/1997 | Klingenstein | |
| 5,702,372 A | 12/1997 | Nelson | |
| 5,752,930 A | 5/1998 | Rise et al. | |
| 5,830,196 A | 11/1998 | Hicks | |
| 5,843,050 A | 12/1998 | Jones et al. | |
| 5,846,220 A | 12/1998 | Elsberry | |
| 5,851,203 A | 12/1998 | van Muiden | |
| 5,899,890 A * | 5/1999 | Chiang et al. | 604/264 |
| 5,947,940 A | 9/1999 | Beisel | |
| 5,961,485 A | 10/1999 | Martin | |
| 5,971,975 A | 10/1999 | Mills et al. | |
| 6,030,369 A | 2/2000 | Engelson et al. | |
| 6,143,013 A | 11/2000 | Samson et al. | |
| 6,197,014 B1 | 3/2001 | Samson et al. | |
| 6,221,059 B1 | 4/2001 | Chiang et al. | |
| 6,258,079 B1 | 7/2001 | Burbank et al. | |
| 6,306,124 B1 | 10/2001 | Jones et al. | |
| 6,436,087 B1 | 8/2002 | Lewis et al. | |
| 6,533,751 B2 | 3/2003 | Cragg et al. | |
| 6,579,484 B1 * | 6/2003 | Tiernan et al. | 264/173.16 |
| 6,596,235 B2 | 7/2003 | Divino, Jr. et al. | |
| 6,622,367 B1 | 9/2003 | Bolduc et al. | |
| 6,652,492 B1 | 11/2003 | Bell et al. | |
| 6,663,614 B1 | 12/2003 | Carter | |
| 2002/0052576 A1 | 5/2002 | Massengale | |

FOREIGN PATENT DOCUMENTS

| | | |
|---|---|---|
| EP | 0 523 928 A2 | 1/1993 |
| EP | 0 452 123 B1 | 1/1996 |
| WO | WO 99/42156 | 8/1999 |

OTHER PUBLICATIONS

Advisory Action mailed Nov. 19, 2008 from corresponding U.S. Appl. No. 10/175,455.

Final Office Action mailed Aug. 7, 2008 from corresponding U.S. Appl. No. 10/175,455.

Office Action mailed Jan. 17, 2008 from corresponding U.S. Appl. No. 10/175,455.

Final Office Action mailed Oct. 24, 2007 from corresponding U.S. Appl. No. 10/175,455.

Office Action mailed Sep. 12, 2005 from corresponding U.S. Appl. No. 10/175,455.

Office Action mailed Aug. 9, 2005 from corresponding U.S. Appl. No. 10/175,455.

Final Office Action for U.S. Appl. No. 10/175,455, filed Jun. 18, 2002, inventor Udo Goebel, Final Office Action mailed Feb. 28, 2006 (10 pages).

Office Action for U.S. Appl. No. 10/175,455, filed Jun. 18, 2002, inventor Udo Goebel, Office Action mailed Jul. 6, 2007 (8 pages).

* cited by examiner

CATHETER

CROSS-REFERENCE TO RELATED APPLICATION

This is a Divisional of application Ser. No. 10/175,455, filed Jun. 18, 2002, which claims priority to German patent Application No. 201 10 121.1, filed Jun. 19, 2001, entitled "CATHETER," the entire contents of each of which are incorporated herein by reference as though set forth in full.

BACKGROUND OF THE INVENTION

The present invention relates to a catheter comprising an elongate tube having a proximal tube portion and a distal tube portion, the distal tube portion forming a catheter tip.

A catheter is a tube which is by a part of its length introduced into the body to establish a liquid or gas connection allowing medicants to be supplied to the body or liquids to be removed therefrom, inter alia. When used for such purposes, the tube has to fulfill special requirements. For instance, the tube must have sufficient stiffness to be advanced into the body. On the other hand, the tip of the catheter must have a suitable degree of softness for precluding injuries to blood vessels or other parts of the body.

EP 0 437 291 B1 describes a known method for producing a soft catheter tip wherein, internally of the catheter tube, a tip of a material of larger softness than the catheter material is molded to the tube. The catheter tip tapers towards the distal end. In this manner, a catheter is obtained whose catheter tip is soft, thus avoiding the risk of inner injuries.

Known from EP 0 452 123 B1 is a catheter comprising a radiopaque halogenated polyurethane. This catheter can comprise a plurality of different materials.

An in-dwelling vein catheter having a conical tip is known from EP 0 523 928 A2. This in-dwelling catheter which is set in the patient's body with the aid of an inserted steel cannula, is made from polyurethane. This material is biocompatible and is commercially available as an optically transparent radiopaque material. The material presents a smooth surface and offers high resistance to buckling.

Catheters with a soft tip are also used in the puncture of central veins. The soft tip is provided to reduce perforations of veins and injuries to the intima. A further application for catheters with soft tips is in epidural anesthesia in order to reduce the occurrence of injuries to vessels or the dura and of paresthesia. In cardiology, use is made of catheters with differently shaped tips so as to be suited to enter the variously shaped veins and arteries.

SUMMARY OF THE INVENTION

It is an object of the invention to provide a catheter which can be inserted into the patient's body in an easier manner and which can be produced with small expenditure.

According to the instant invention, the above object is achieved by the features indicated in claim 1. As set out in the claim, the distal tube portion of the catheter as compared to the proximal tube portion has a reduced outer diameter. The reduction of the outer diameter of the distal tube portion can be obtained by stretching or drawing the catheter material, with the catheter being extended and thus plastically deformed. In the process, the length of the distal tube portion is increased, and the outer diameter is reduced by lateral contraction. The tube is made throughout of the same tube material and is deformed only by extension. This obviates the need to connect two different materials with each other.

By subjecting the distal tube portion to stretching, this portion is given increased softness and deformability. Advancing the distal tube portion over a guide wire as well as pushing it through a cannula are facilitated.

The invention provides a catheter comprising a highly flexible, soft distal tube portion and a stable proximal tube portion with good pushability while making it possible to use one base material for the overall catheter.

The stretching of the catheter can be followed by an after-treatment of the distal tube portion which will be cut to the desired length or be formed with roundnesses. Further, the distal tube portion can be provided with perforations.

The principle of the present invention finds preferred application in catheters for regional anesthesia, particularly for spinal anesthesia, which are introduced into the spinal marrow; catheters for epidural anesthesia which are set in the epidural space beside the spinal marrow; and in plexus catheters. These catheters are used in connection with a complementary regional-anesthesia cannula, particularly a spinal-anesthesia cannula, an epidural cannula or a plexus cannula.

The tapered distal tube portion is preferably substantially cylindrical and has a length at least five times and preferably at least ten times as large as the outer diameter of the proximal tube portion. This means that not only the catheter tip but the whole distal tube portion is reduced in diameter.

BRIEF DESCRIPTION OF THE DRAWINGS

Embodiments of the invention will be explained in greater detail hereunder with reference to the accompanying drawings.

DETAILED DESCRIPTION OF THE DISCLOSURE

Figure 1:
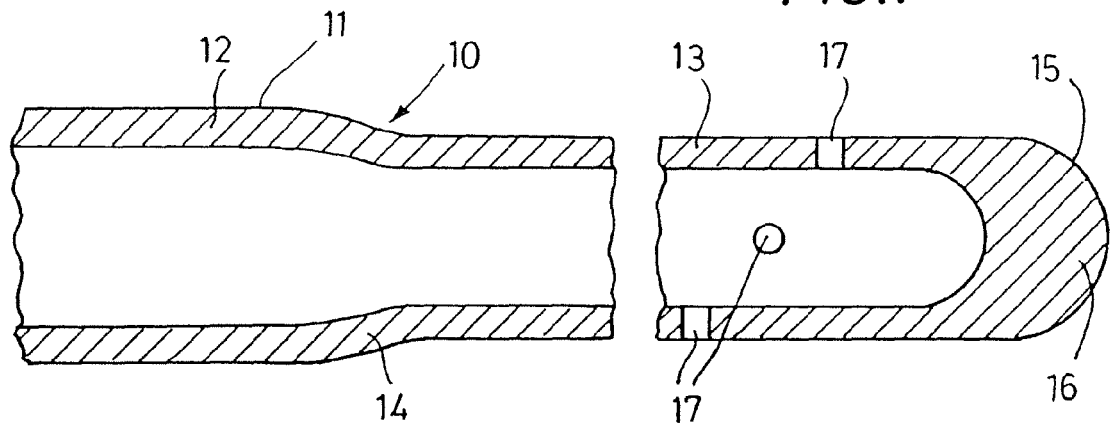
FIG. 1 is longitudinal sectional view of an epidural catheter according to the present invention with closed catheter tip.

The catheter 10 shown in FIG. 1 is an epidural catheter as used in regional anesthesia for injection of a local anesthetic e.g. into the epidural space. Catheter 10 comprises an elongate tube 11 made of the same material throughout its length. Tube 11 comprises a proximal tube portion 12 and a distal tube portion 13. The total length of the catheter is 1000 mm. Proximal tube portion 12 has an outer diameter of 0.85 mm and an inner diameter of 0.45 mm. These specifications are only examples while, of course, also other dimensions are possible.

The distal tube portion 13 has a length of at least 10 mm. The outer diameter of distal tube portion 13 is reduced to about 80% of the outer diameter of the proximal tube portion 12, but may range anywhere from about 50%-90% of the outer diameter of the proximal tube portion. This reduction is effected by stretching while a transition region 14 is generated in the process. The stretching is performed by pulling the tube in the longitudinal direction, with its proximal tube portion 12 fixed in position by a clamping device while the distal tube portion 13 is pulled to thus extend its length. If required, a suitable mandrel can be used to assist in the stretching. When the distal tube portion 13 is pulled to assume a larger length, the wall thickness of distal tube portion 13 is reduced by lateral contraction. Arranged on the distal end of distal tube portion 13 is the catheter tip 15 which in the present example is formed by a round end cap 16 made from the catheter material. Alternatively, a central opening can be formed on the tip of the catheter. In the catheter 10 of FIG. 1, lateral openings 17 are provided on the distal tube portions near the catheter tip, allowing liquid to pass therethrough out of the catheter.

Figure 2:
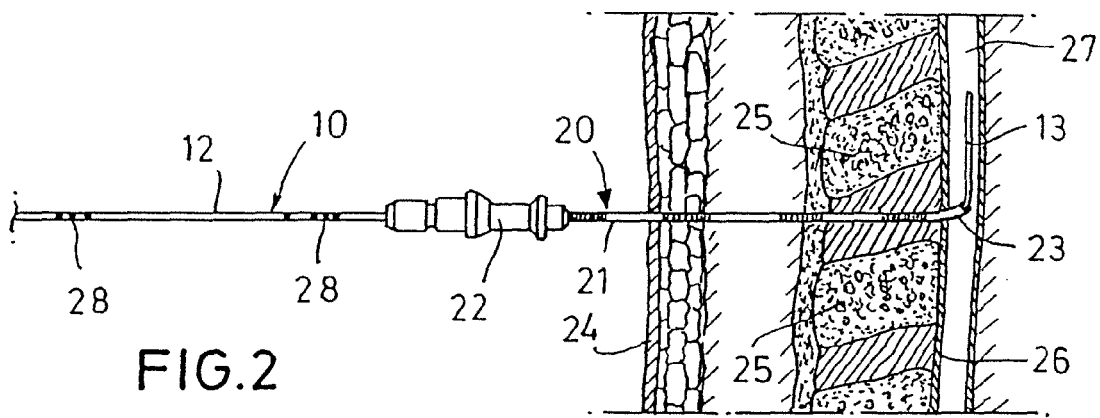
FIG. 2 is a view illustrating the use of a catheter according to FIG. 1 in connection with a Tuohy cannula.

FIG. 2 illustrates the use of catheter 10 as an epidural catheter. Catheter 10 is used in connection with a Tuohy cannula. The latter comprises a steel cannula 21 having its proximal end provided with a cannula hub 22. The distal end of cannula 21 is formed with a bend 23. As depicted in FIG. 2, the cannula 20 is advanced trough the skin 24, between the vertebrae 25 of the spinal column, through the ligamentum flavum 26 and into the epidural space 27. Then, catheter 10 is advanced through cannula 20. While passing through the curved end 23 of cannula 20, the catheter 10 is caused to follow the angle of the cannula end 23 and will then be further advanced into the epidural space 27. Thereafter, cannula 20 is withdrawn from catheter 10, and the catheter is ready for injection of a local anesthetic therethrough into the epidural space 27. In the present embodiment, the tapered distal tube portion 13 has a length of about 5 cm. This length corresponds to the length projecting beyond the cannula end 23 into the epidural space. The proximal tube portion 12 is provided with markings 28 for determining the insertion depth of the catheter.

Figure 3:
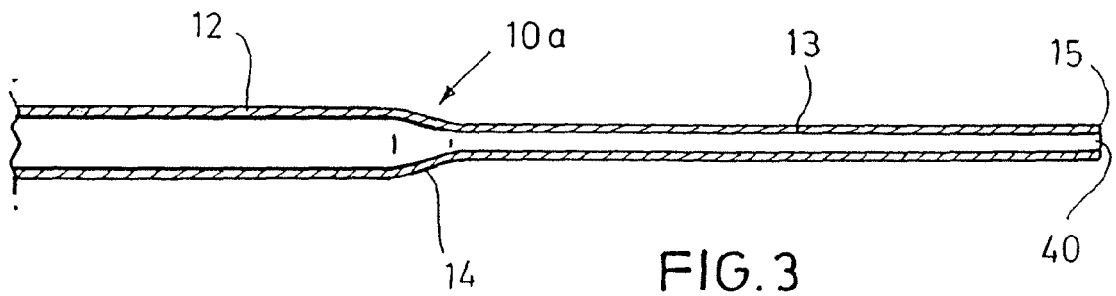
FIG. 3 is longitudinal sectional view of a catheter for central veins.
Figure 4:
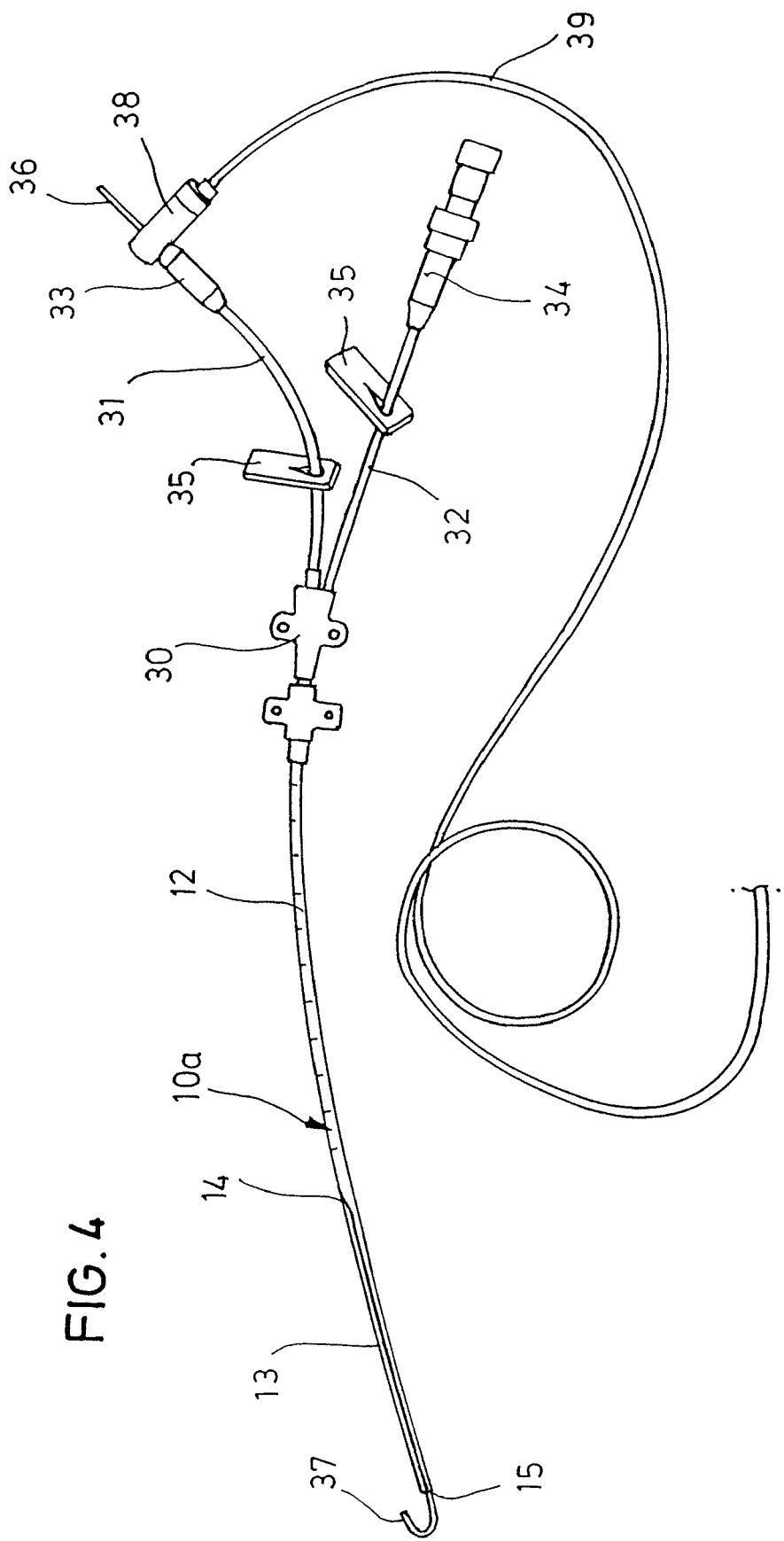
FIG. 4 is an overall view of the above catheter for central veins.

FIG. 3 shows a catheter 10a for use as a central-vein catheter, which may also be an in-dwelling type catheter. This catheter will be set through a central vein up to the immediate vicinity of the heart, with the catheter tip 15 being first advanced into the right-hand vestibulum under ECG position control and then being withdrawn into the hollow vein. Subsequently, a medicant will be injected through the catheter into the hollow vein. The catheter includes a guide wire whose tip emerges at the catheter tip 15 and a catheter tip central opening 40 with a rounded opening edge. Delivery of the picked-up ECG signals is performed via the guide wire.

The total length of catheter 10a is about 15 cm in case of a central-vein catheter.

Catheter 10a comprises a proximal tube portion 12 and a distal tube portion 13 of a tapered shape relative to proximal tube portion 12. Both tube portions 12 and 13 are made throughout of the same materials. Distal tube portion 13 has a length of at least 10 cm.

Catheter 10a is connected to a Y-piece 30 having two branches 31 and 32 originating therefrom. Branch 31 is connected to a catheter hub 33, and branch 32 is connected to a catheter hub 34. Each of branches 31 and 32 is provided with a tube clamp 35. A guide wire 36 is arranged to pass through branch 31 and catheter 10a, presenting at its distal end an easily deformable curved tip 37 arranged to project from catheter tip 15. The distal end of guide wire 36, projecting from catheter hub 33, is connected by means of a contact clamp 38 to a cable 39 adapted for connection to an ECG display unit. In this manner, it can be observed by ECG control whether the catheter tip is arranged in the right-hand vestibulum or in the hollow vein.

Guide wire 36 has a diameter allowing it to be advanced through the distal tube portion 13 without notable friction. The wire will issue from the central opening at the catheter tip 15. The edges of the opening are rounded.

Catheter 10a which in the present embodiment has a sole lumen, can also be formed to have plural lumina. By the stretching of distal tube portion 13, all of the lumina will be reduced in diameter.

The catheter is made of the same material throughout its length. By way of alternative, the catheter can also be a two- or multi-layered configuration and comprise an inner tube and an outer tube, and the catheter can be produced especially by coextrusion of both tubes.

Particularly useful for an epidural catheter is the material combination PA-PU, the inner tube made from polyamide and the outer tube made from polyurethane. Of particular usefulness for a central-vein catheter is the material combination PU-PU of different polyurethanes, and for an in-dwelling vein cannula a material combination PA-PA of different polyamides is preferred.

What is claimed is:

1. A method for forming a catheter for use with a cannula comprising:
   co-extruding a tube comprising an outer layer of a first material and an inner layer of a second material to a first outside diameter and first inside diameter;
   subsequent to the co-extruding step, holding a section of the tube and stretching a portion of the tube to form a distal tube portion and a proximal tube portion having a transition zone therebetween;
   wherein an inside diameter of the distal tube portion is smaller than the first inside diameter after the stretching step; and
   wherein a distal end of the distal tube portion comprises a round enclosed end cap.

2. The method of claim 1, wherein the outer layer is made from polyurethane.

3. The method of claim 2, wherein the inner layer is made from polyamide.

4. The method of claim 1, wherein the inner layer is made from polyamide.

5. The method of claim 1, wherein the catheter is an epidural catheter.

6. The method of claim 1, further comprising a plurality of lateral openings.

7. The method of claim 1, wherein the transition zone has a first thickness along a proximal end of the transition zone and a second thickness along a distal end of the transition zone and wherein the first thickness is greater than the second thickness.

8. The method of claim 1, wherein the co-extruded distal tube portion comprises a wall thickness that is less than a wall thickness of the co-extruded proximal tube portion.

9. The method of claim 1, further comprising providing the proximal tube portion with a plurality of markings.

10. A method for forming a catheter for use with a cannula comprising:
    forming a catheter comprising an inner elongate tube and an outer elongate tube throughout a proximal tube portion and a distal tube portion, the distal tube portion having an enclosed end cap;
    wherein both the inner and the outer elongate tubes of the distal tube portion have a smaller inside diameter than an inside diameter of the proximal tube portion, which is made smaller by stretching the distal tube portion subsequently to forming the catheter and forming a transition zone therebetween; and
    inserting the catheter inside a lumen of a cannula on that at least some of the distal tube portion of the catheter extends beyond the end opening of the cannula.

11. The method of claim 10, wherein the outer elongate tube is made from polyurethane.

12. The method of claim 10, wherein the inner elongate tube is made from polyamide.

13. The method of claim 10, wherein the catheter is an epidural catheter.

14. The method of claim 10, wherein the distal end of the distal tube portion further comprises a plurality of lateral openings.

15. The method of claim 10, wherein the transition zone has a first thickness along a proximal end of the transition zone and a second thickness along a distal end of the transition zone and wherein the first thickness is greater than the second thickness.

16. The method of claim 10, wherein the distal tube portion comprises a wall thickness that is less than a wall thickness of the proximal tube portion, which is made less by stretching.

17. The method of claim 10, further comprising providing the proximal tube portion of the catheter with a plurality of markings.

18. The method of claim 10, wherein the cannula is made of metal and has a curved tip.

19. The method of claim 18, wherein the cannula is a Tuohy cannula.

* * * * *

UNITED STATES PATENT AND TRADEMARK OFFICE
CERTIFICATE OF CORRECTION

PATENT NO. : 7,763,196 B2
APPLICATION NO. : 11/875296
DATED : July 27, 2010
INVENTOR(S) : Udo Goebel et al.

It is certified that error appears in the above-identified patent and that said Letters Patent is hereby corrected as shown below:

In column 4, line 65, in claim 10, delete "on" and insert -- so --, therefor.

Signed and Sealed this

Fourteenth Day of December, 2010

David J. Kappos
*Director of the United States Patent and Trademark Office*